United States Patent [19]
LeVantine

[11] 3,984,157
[45] Oct. 5, 1976

[54] COAXIAL OPTHALMOSCOPE ARRANGEMENT

[75] Inventor: Allan D. LeVantine, Tarzana, Calif.

[73] Assignee: Cavitron Corporation, N.Y.

[22] Filed: Feb. 13, 1974

[21] Appl. No.: 441,951

[52] U.S. Cl. .................................. 351/9; 351/12
[51] Int. Cl.² ........................................ A61B 3/12
[58] Field of Search ............... 351/6, 9, 12, 16, 10, 351/11, 13, 15

[56] References Cited
UNITED STATES PATENTS

| 1,128,859 | 2/1915 | DeZeng | 351/12 |
| 1,795,691 | 3/1931 | Wilson | 351/12 |
| 1,859,756 | 5/1932 | Tillyen | 351/9 |
| 1,889,456 | 11/1932 | Tillyer | 351/9 X |
| 2,221,928 | 11/1940 | Rimington | 351/13 |
| 3,602,581 | 8/1971 | Heine | 351/16 X |

OTHER PUBLICATIONS

*Essentials of Ophthalmology,* Roland I. Pritikin, C1950 (received 11-7-51 Patent Office) p. 132.

*Primary Examiner*—Paul A. Sacher
*Attorney, Agent, or Firm*—Don B. Finkelstein

[57] ABSTRACT

An improved coaxial ophthalmoscope incorporating a light trap for absorbing substantially all of the light not utilized for illuminating the retina of the eye under examination and thereby preventing the unused light from reflecting back into the eye of the viewer thus obscuring the vision thereof.

12 Claims, 5 Drawing Figures

3,984,157

COAXIAL OPTHALMOSCOPE ARRANGEMENT

BACKGROUND OF THE INVENTION

1. Field of the Invention

This invention relates to the opthalmoscope art and more particularly to an improved coaxially ophthalmoscope having an improved light trap for preventing reflection of unused light into the eye of the viewer.

2. Description of the Prior Art

Ophthalmoscopes utilized for examining the interior structure of an eye have long been know. One class of such ophthalmoscopes is termed coaxial ophthalmoscopes and in such coaxial ophthalmoscopes the axis of viewing the eye under examination coincides with the axis of the light directed into the eye under examination. The advantages of such a coaxial arrangement are, of course, well known in the art. However, in order to provide such a coaxial viewing of the eye under examination it is necessary that the portion of the generated light not directed to the eye under examination be substantially absorbed in order to prevent reflection of this light back into the eye of the viewer. Such devices for absorbing light are generally termed light traps.

The U.S. Pat. Nos. to Tillyer, 1,664,953 and 1,859,756 both show essentially coaxial ophthalmoscope arrangement incorporating a light trap. However, the light trap shown therein has not proven to be sufficiently effective in preventing transmission of the unused portion of the light back into the eye of the viewer.

Similarly, in Tillyer, U.S. Pat. No. 1,889,456 there is a light trap similar to that shown in U.S. Pat. No. 1,859,756.

Other ophthalmoscope arrangements are shown in U.S. Pat. Nos. 3,524,702; 3,543,746; 3,572,910; 3,586,424; 3,600,067 and 3,602,581. However, in none of these patents is there a recognition of the problem inherent in allowing unused light to reflect back into the eye of the viewer nor the necessity for absorbing substantially all of such unused light.

SUMMARY OF THE INVENTION

Accordingly, it is an object of the present invention to provide an improved ophthalmoscope.

It is another object of the present invention to provide an improved coaxial ophthalmoscope.

It is another object of the present invention to provide an improved coaxial ophthalmoscope in which substantially all of the light not utilized for illuminating the eye under examination is prevented from reflecting into the eye of the viewer.

The above and other objects of the present invention are achieved, according to a preferred embodiment thereof, by providing an elongated casing that may be hand held during examination of an eye. The casing contains therein a light beam generating means for generating a beam of visible light in a first direction along a first axis. The light beam generating means, for a portable embodiment of the present invention, incorporates a source of electrical energy such as a battery together with a means for generating a beam of visible light such as a lightbulb interconnected by an on-off switch. Suitable optical means which may include apertures, lenses or the like direct the beam of light along the first axis to a beam splitter which, in preferred embodiment of the present invention comprise one or more optically transparent rectangular parallelopiped members. For example, it has been found that conventional cover glasses on the order of 0.006 to 0.020 inches thick can be utilized in the present invention as a beam splitter. Alternatively, a half silvered glass member or other types of conventional beam splitters may be utilized. The beam splitter is preferably oriented at 45° to the first axis and, due to first and second surface reflections, redirects a first preselected amount of the light generated by the lightbulb into a second direction on a second axis. The second direction is substantially at right angles to the first direction and the first portion of light is directed out of the ophthalmoscope into the eye under examination. An exit aperture is provided in the casing means for allowing the first portion of the light to exit therefrom into the eye under examination. Coaxially aligned with the exit aperture is a viewing aperture on the opposite side of the beam splitter to allow viewing of the eye under examination through the second aperture, through the beam splitter and through the exit aperture. A diopter wheel, which is well known in the art, may also be incorporated exterior to, and on the viewing side of the casing means for interposing the required magnification for viewing the eye.

A second portion of the light beam that has been generated is transmitted through the beam splitter means and comprises substantially all of the light that is not directed into the eye under examination. The second portion of the light impinges upon a light trap means spaced from the beam splitter means and position to receive the second portion of the light beam. The light trap means absorbs substantially all of the second portion of light and prevents substantially any of the second portion of light from being reflected back onto the beam splitter means where it may be reflected into the eye of the viewer and thus obscure a clear vision of the eye under examination.

In a preferred embodiment of the present invention the light trap means generally comprises a wedge-shaped optically transparent body member provided with a first planar surface for receiving the second portion of the light and the first planar surface is positioned at a preselected angle to the first axis. The preselected angle is selected to prevent direct reflection from the first planar surface of the light trap means through the second aperture into the eye of the viewer. This angle may be, for example, on the order of 36°. The light trap means also has a base planar surface substantially parallel to the first axis and intersecting the first planar surface at a first edge. An outer planar surface intersects the base planar surface at a second edge to define a second preselected angle therewith and also intersects the first planar surface at a third edge to define a third preselected angle therewith. The second and third preselected angles are selected to give a predetermined number of internal reflections within the light trap means for light entering from the first planar surface. For example, the predetermined number of internal reflections may be seven. Parallel to the first axis are a pair of spaced apart substantially parallel planar side surfaces on the light trap means and all of the surfaces except the first planar surface receiving the second portion of the light are coated with a flat black coating to substantially reduce internal reflections and to minimize transmission therethrough and reflection therefrom during the preselected number of internal reflections.

When the index of refraction of the optically transparent body member is on the order of 1.49, the first planar surface intersects the outer planar surface at an angle of approximately 17° and the base planar surface intersects the outer planar surface at approximately 18°. At such a 36° angle of the first planar surface with the first axis, there will be approximately seven per cent (7 percent) of the light reflected out of the field of view by first surface reflection of the first planar surface. In order to reduce even further the amount of first surface reflection, in another embodiment of the present invention, two such wedge shaped optically transparent body members may be positioned as a light trap with the base planar surfaces of each coaxially aligned with the first axis. In such an arrangement it has been found that, with an internal reflection from the flat black surfaces of approximately 0.02 and there are seven internal reflections, the amount of light that could be reflected back to the beam splitter and out into the eye of the viewer will be approximately $1.28 \times 10^{-12}$ of the amount of incident light on the first planar surface. This would be true for both the single wedge light trap and the double wedge light trap described above. The double wedge light trap, of course, provides the advantage of reducing the size of the unit as well as minimizing the amount of the first surface reflection that could reflect back into the eye of the viewer.

BRIEF DESCRIPTION OF THE DRAWING

The above and other embodiments of the present invention may be more fully understood from the following detailed description taken together with the accompanying drawings wherein similar reference characters refer to similar elements throughout and in which.

DESCRIPTION OF THE PREFERRED EMBODIMENTS

Figure 1:
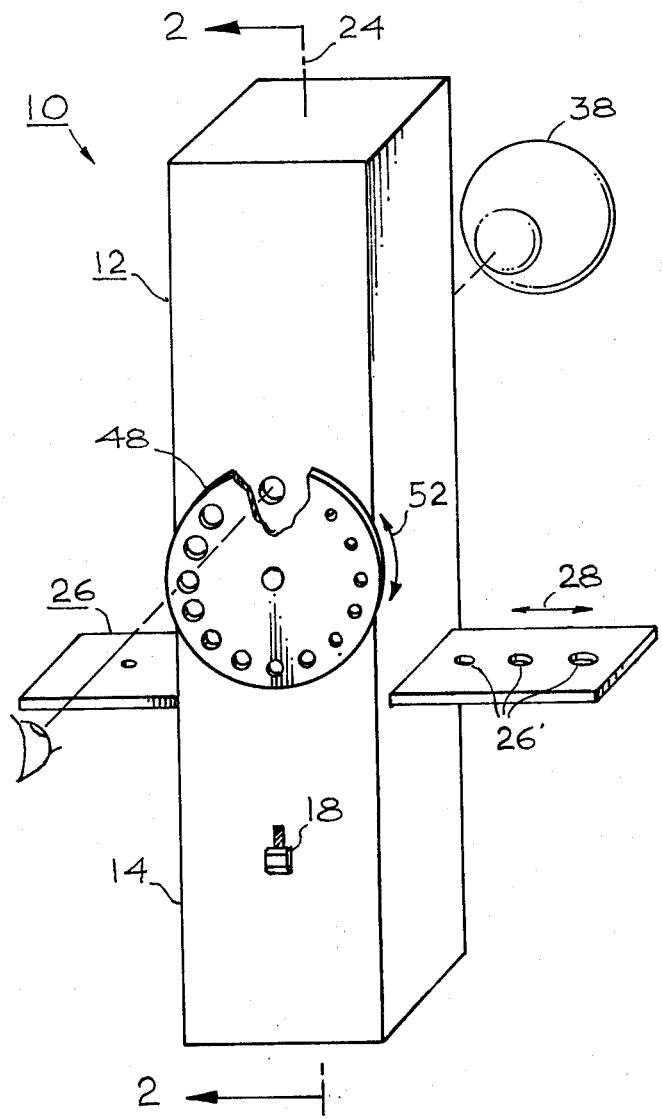
FIG. 1 is a perspective view of a preferred embodiment of the present invention.
Figures 2, 3:
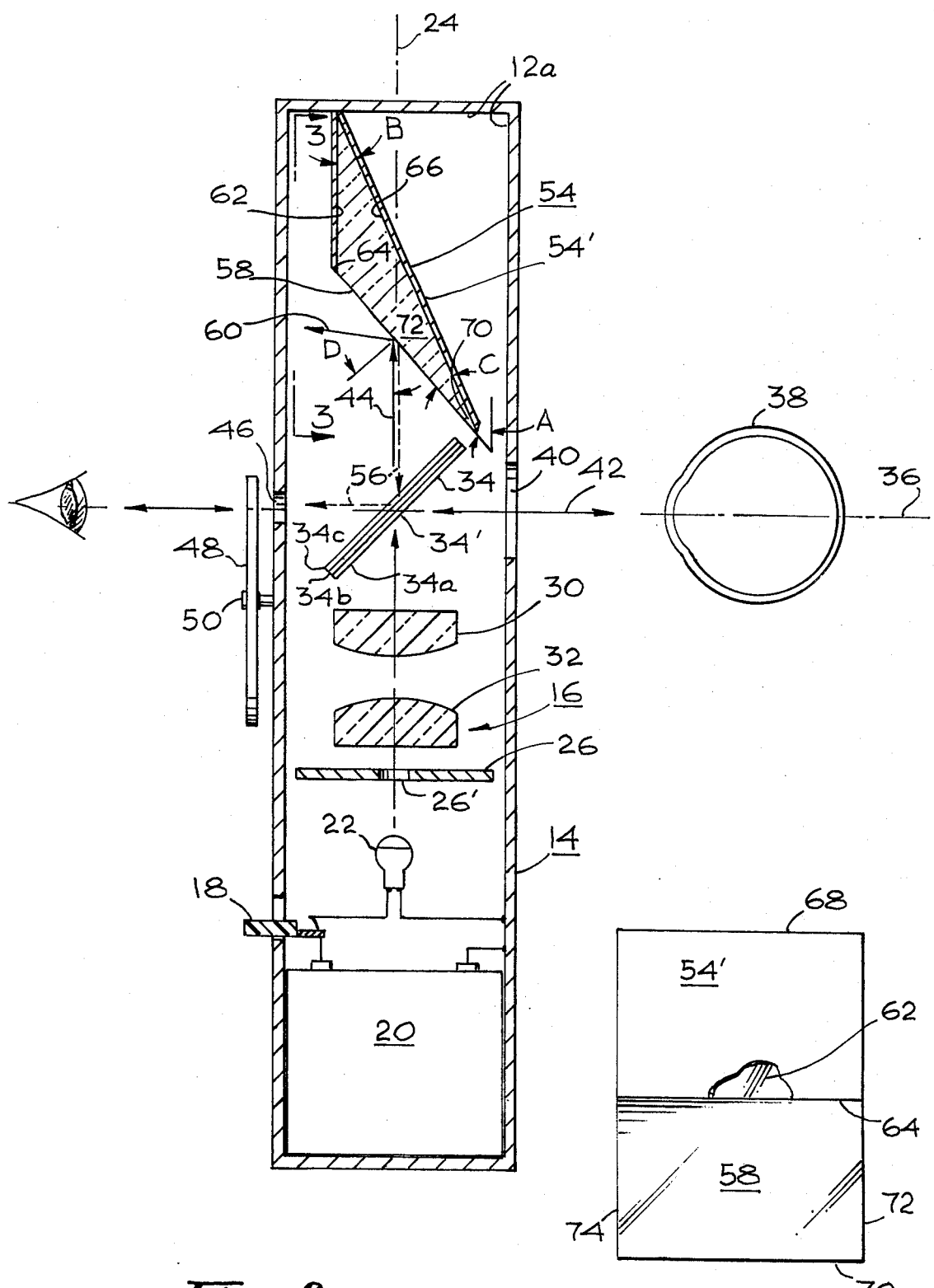
FIG. 2 is a sectional view along the line 2—2 of FIG. 1.
FIG. 3 is a view along the line 3—3 of FIG. 2.

Referring now to the drawing and in particular FIGS. 1, 2 and 3 thereof there is illustrated a preferred embodiment generally designated 10 of an improved coaxial ophthalmoscope. The embodiment 10 generally comprises an elongated case member 12 having a lower portion 14 which, in utilization of the embodiment 10 may be utilized to hold the ophthalmoscope 10. Contained within the case means 14 is a light beam generating means generally designated 16 having an on-off switch 18 controlling the flow of electrical energy from a source of electrical energy such as the battery 20 to a lightbulb 22 which, if desired, may incorporate a lens portion 22'.

Light from the lightbulb 22 is directed in a first direction along a first axis 24 through, for example, a sliding aperture plate 26 having a plurality of apertures 26' therethrough that may move in the direction indicated by the arrow 28 to select the diameter of the light beam projected to the eye 38 from the lightbulb 22. One or more lenses, such as lenses 30 and 32, may also be incorporated in the light beam generating means as well as any other type of optical train desired. The light from the lightbulb 22 is thus directed onto a beam splitter 34 positioned within the case means 12 and, in preferred embodiments of the present invention positioned to intercept the light transmitted thereto by the light beam generating means 16 and, preferably, is positioned at an angle of approximately 45° to the direction of the first axis 24.

In this preferred embodiment 10 of the present invention the beam splitter means 34 comprises one or more rectangular parallelopiped members and three such members 34a, 34b and 34c are shown in the embodiment 10. However, it will be appreciated that one such member may also be utilized as well as more than three. Each of the members 34a, 34b and 34c are optically transparent planar members each having a thickness on the order of, for example, 0.006 inches. At an angle of 45° the first member 34a reflects approximately 10 percent of the light received thereon from the light beam generating means in a second direction along a second axis generally designated 36 into an eye 38 that is to be examined. Similarly, when two members 34a and 34b are utilized an additional portion of the light generated by light generating means 16 will be reflected along the second axis 36 by the interface between the two members and thus a total of approximately 19 percent of the light may be transmitted therethrough. With three members 34a, 34b and 34c an additional portion of the light will also be directed from the interface between the members 34b and 34c along the second axis 36 into the eye 38 being examined.

It will be appreciated that other types of beam splitters may be utilized in the practice of the present invention. For example, instead of one or more thin glass members, a one-half silvered glass may be utilized as a beam splitter, or other conventional beam splitters.

Thus, the amount of light reflected by the beam splitter means 34 through exit aperture 40 in the case means 12 and into the eye under examination 38 comprises a first preselected portion 42. The remainder of the light generated by the light beam generating means 16 is transmitted through the beam splitter 34 along the first axis 24 and comprises a second preselected portion 44 thereof.

A viewing aperture 46 is provided in the case means 12 substantially coaxially aligned with the exit aperture 40 to allow viewing along the second or viewing axis 36 through the beam splitter means 34 and into the eye 38 under examination. Thus, viewing along the second or viewing axis 36 is coaxial with the second direction of the light 42 therealong entering the eye under examination 38. A diopter wheel of conventional design 48 may also be incorporated if desired and is pivotally mounted on pin 50 for rotation in the direction indicated by the double-ended arrow 52. The diopter wheel and its design are well known in the art and do not, per se, form a portion of applicant's invention herein.

The second preselected portion of light 44 transmitted through the beam splitter means 34 is received by a light trap means 54 and, in accordance with the principles of the present invention, the light trap means 54 absorbs substantially all of the second preselected amount of light 44 and prevents same from being reflected back through the viewing aperture 46 and into the eye of the viewer, as indicated by the dotted arrows 56 in FIG. 2. In order to achieve the virtual elimination of any of the second portion amount of light 44 from being reflected into the eye of the viewer through the viewing axis 46 and thus tending to obscure the desired view of the eye 38 under examination, it has been found that the light trap means 54 may take the form of an optically transparent wedgeshaped member having a first planar surface 58 that receives the second preselected amount of light 44 thereon. The first planar surface 58 is oriented at a first preselected angle A to the first preselected axis 24. The angle A may be selected to prevent first surface reflection, indicated by the arrow 60, from reflecting into the viewing aperture 46. The internal surfaces 12a of the case means 12 may be coated with, for example, a flat black paint to minimize surface reflections therefrom and thus minimize any stray reflections that might tend to be reflected through the viewing aperture 46.

The light trap means 54 also comprises a base planar surface 62 substantially parallel to the first axis 24 intersecting the first planar surface at a first edge 64. The base planar surface 62, as noted above, extends parallel to the first axis 24 and the base planar surface 62 intersects an outer planar surface 66 at a second preselected angle B at a second edge 68 thereof. The outer planar 66 also intersects the first planar surface 58 at a third edge 70 at an angle C. As shown more clearly in FIG. 3 the light trap 54 also has a pair of spaced apart substantially parallel planar side surface 72 and 74.

All the planar surfaces of the light trap 54 except the first planar surface 58 are preferably coated with a flat black paint to minimize the percentage of light internally reflected therefrom.

For a given number of reflections N, the equation for determining the value of the angle B is shown below as Equation 1:

$$B = \frac{2(A + \phi')}{N + 1} \quad \text{Equation 1}$$

where: $\phi = (\pi/2 - A)$,
the angle of incidence at the first surface
$\phi' =$
angle of refraction inside first surface and from Equation 2:

$$\sin\phi' = \frac{\sin\phi}{n} \quad \text{Equation 2}$$

where: $n =$ index of refraction

Thus, for a light trap 54 having an index of refraction $n$ of 1.49, and $A = 36°$ the angle B for a total of seven internal reflections is on the order of 17.225° and, consequently, the angle C is on the order of 18.775°.

With the planar surfaces coated above, the internal reflections therefrom at each of the seven reflections will be approximately 0.02 and therefore the total amount of light, represented by the arrow 56, reflected back into the eye of the viewer is approximately $(0.02)^7$ or $1.28 \times 10^{-12}$ of the second preselected amount of light indicated by the arrow 44. Thus, substantially all of the second preselected amount of light has been internally absorbed in the light trap 54 and virtually no light is reflected back into the eye of the observer through the viewing aperture 46.

Figure 4:
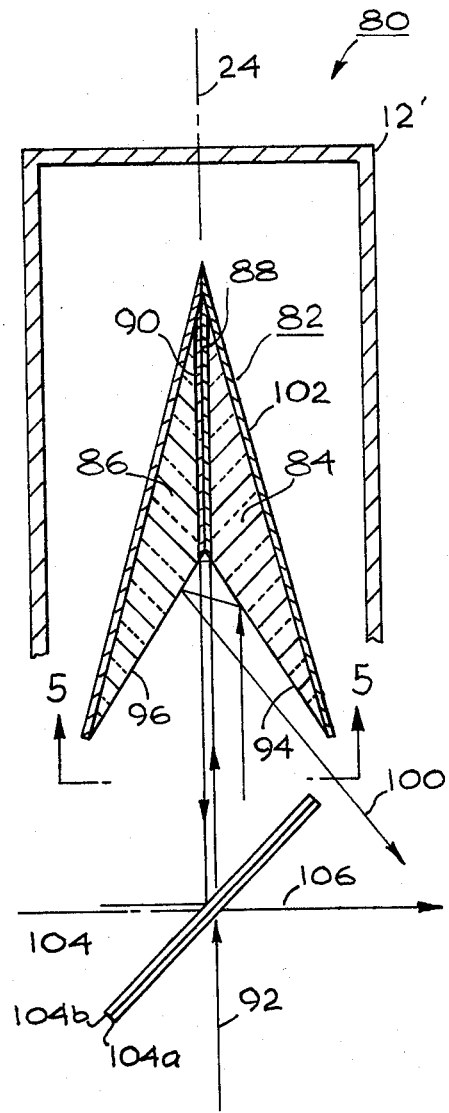
FIG. 4 illustrates another embodiment of the present invention.
Figure 5:
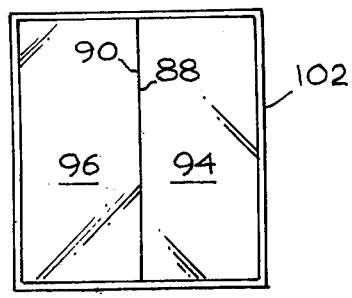
FIG. 5 is a sectional view along the line 5—5 of FIG. 4.

In order to reduce even further the possibility of first surface reflection from the light trap entering the viewing aperture 46, it may be desirable to provide a light trap comprising two wedge-shaped body members each substantially identical to the light trap 54. Such an embodiment, generally designated 80, is shown in FIGS. 4 and 5 wherein a case means 12 essentially identical to the case means 12 described above is provided in a coaxial ophthalmoscope. In this embodiment the light trap 82 is generally comprised of two wedge-shaped members 84 and 86 each substantially identical to the wedge-shaped body member 54 described above. However, in the light trap 82 the base surface 88 of the first wedge-shaped member 82 and the base surface 90 of the second wedge-shaped member 86 are bonded together and lie coaxially along the first axis 24' which is the axis along which the beam of visible light indicated by the arrow 92 is generated by a light beam generating means (not shown in FIG. 4) but which is similar to the light beam generating means 16 described above.

The first planar surface 94 of the first wedge-shaped member 82 and the first planar surface of the second wedge-shaped member 86 are each at an angle of approximately 36° to the direction of the first axis 24'. It has been found that this angle provides the first surface reflection light from the first planar surfaces 94 and 96 will strike the opposite first planar surface and be reflected therefrom at an angle substantially parallel to the first planar surface that the light is reflected from. The effect of these two first surface reflections is that the total first surface reflected light is the product of the two first surfaces or $0.07 \times 0.04 = 0.0028$. This is indicated by the arrow 100 in FIG. 4. A flat black coating 102 is provided on all surfaces of the first wedge-shaped body member 84 and second wedge-shaped body member 86 except the first planar surfaces 94 and 96, respectively thereof.

In the embodiment 80 shown in FIG. 4 the beam splitter means 104 comprises only two rectangular parallelopiped members 104a and 104b for reflecting the first preselected amount of light indicated by the arrow 106 in a second direction along a second axis 108 in a manner similar to that described above.

With the light trap means 82 shown in FIG. 4 the first surface reflection indicated by the arrows 100 is reduced to $(0.07)(0.04) = 0.0028$.

From the above it is apparent that there has been described a structure for an improved coaxial ophthalmoscope in which virtually all of the light not utilized for examination of the eye under examination is internally absorbed and virtually none of the light that is not utilized in illuminating the eye under examination is reflected back into the eye of the viewer. Those skilled in the art may find many variations and adaptations and the appended claims are intended to cover all such structure falling within the true scope and spirit thereof.

I claim:

1. In a coaxial ophthalmoscope of the type in which the viewing axis is coaxially aligned with a beam of light directed into the eye under examination the improvement comprising:

light beam generating means for generating a beam of visible light in a first direction along a first axis;

beam splitter means spaced from said light beam generating means and positioned to intercept said beam of light and reflect a first preselected amount thereof in a second direction, different from said first direction, along a viewing axis, and transmit a second preselected amount of said beam of visible light therethrough along said first axis;

light trap means spaced from said splitter means and comprising a first planar surface means free of light absorbing coating thereon spaced from said beam splitter means and positioned at a predetermined angle to said first axis to receive said second preselected amount of said beam of light transmitted through said beam splitter means, and said light trap means for preventing substantially all of said second preselected amount from reflecting along said viewing axis;

means for directing said first preselected amount of said beam of light into an eye under examination; and means for viewing said eye under examination through said beam splitter along said viewing axis.

2. The arrangement defined in claim 1 wherein: said first preselected amount of said beam of light reflected along said viewing axis comprises approximately 15 percent to 30 percent of said beam of light, and said second preselected amount of said beam of light transmitted through said beam splitter correspondingly comprises approximately 85 percent to 70 percent thereof.

3. The arrangement defined in claim 1 wherein said light trap means further comprises:
an optically transparent body member having:
said first planar surface at a first preselected angle to said first axis;
a base planar surface substantially parallel to said first axis and intersecting said first planar surface at a first edge;
an outer planar surface intersecting said base planar surface at a second edge and defining a second preselected angle therewith and intersecting said first planar surface at a third edge to define a third preselected angle therewith; and
a pair of spaced apart substantially parallel planar side surfaces intersecting said base planar surface, said outer planar surface, and said first planar surface.

4. The arrangement defined in claim 3 wherein said light trap means is solid and further comprises:
a flat black coating on said base planar surface, said outer planar surface and said side planar surfaces.

5. The arrangement defined in claim 4 wherein:
said first preselected angle is on the order of 36°, said second preselected angle is on the order of 17° and said third preselected angle is on the order of 18°; and
the index of refraction of said body member is on the order of 1.49.

6. The arrangement defined in claim 1 wherein said light trap means further comprises:
a pair of optically transparent substantially identical body members, each of said pair of body members having:
said first planar surface for receiving approximately 50 percent of said second preselected amount of said light, and said first planar surface at a first preselected angle to said first axis;
a base planar surface substantially parallel to said first axis and intersecting said first planar surface at a first edge;
an outer planar surface intersecting said base planar surface at a second edge to define a second preselected angle therewith and intersecting said first planar surface at a third edge to define a third preselected angle therewith; and
a pair of spaced apart substantially parallel planar side surfaces;

said base planar surfaces of each of said pair of body members substantially coextensive and contiguous and aligned along said first axis.

7. The arrangement defined in claim 6 and further comprising:
a black coating on said base planar surface, said outer planar surface and said side planar surfaces on each of said pair of body members.

8. The arrangement defined in claim 7 wherein:
said first preselected angle is on the order of 36°, said second preselected angle is on the order of 17° and said third preselected angle is on the order of 18°; and
the index of refraction of each of said pair of body members is on the order of 1.49.

9. The arrangement defined in claim 1 wherein said beam splitter means further comprises:
at least one optically transparent, right rectangular parallelopiped member having a thickness of approximately 0.006 to 0.020 inches and positioned at approximately 45° to said first axis; and
said second direction along said viewing axis is substantially perpendicular to said first direction along said first axis.

10. The arrangement defined in claim 1 wherein said beam splitter means further comprises:
a plurality of stacked optically transparent right rectangular parallelopiped members each having a thickness of approximately 0.006 to 0.020 inches and positioned at approximately 45° to said first axis; and
said second direction along said viewing axis is substantially perpendicular to said first direction along said first axis.

11. The arrangement defined in claim 9 wherein said light trap means further comprises:
an optically transparent body member having:
said first planar surface at a first preselected angle to said first axis;
a base planar surface substantially parallel to said first axis and intersecting said first planar surface at a first edge;
an outer planar surface intersecting said base planar surface at a second edge and defining a second preselected angle therewith and intersecting said first planar surface at a third edge to define a third preselected angle therewith; and
a pair of spaced apart substantially parallel planar side surface intersecting said base planar surface, said outer planar surface, and said first planar surface.

12. The arrangement defined in claim 9 wherein said light trap means further comprises:
a pair of optically transparent substantially identical body members, each of said pair of body members having:
said first planar surface for receiving approximately 50 percent of said second preselected amount of said light, and said first planar surface at a first preselected angle to said first axis;
a base planar surface substantially parallel to said first axis and intersecting said first planar surface at a first edge;
an outer planar surface intersecting said base planar surface at a second edge to define a second preselected angle therewith and intersecting said first planar surface at a third edge to define a third preselected angle therewith; and
a pair of spaced apart substantially parallel planar side surfaces;
said base planar surfaces of each of said pair of body members substantially coextensive and contiguous and aligned along said first axis.

* * * * *